United States Patent [19]

Alexander et al.

[11] 4,001,270
[45] Jan. 4, 1977

[54] 9-BENZOYL-1,2,3,4-TETRAHYDROCAR-BAZOLE

[75] Inventors: Ernest John Alexander, East Greenbush; Aram Mooradian, Schodack, both of N.Y.

[73] Assignee: Sterling Drug Inc., New York, N.Y.

[22] Filed: Dec. 12, 1975

[21] Appl. No.: 640,249

Related U.S. Application Data

[63] Continuation-in-part of Ser. No. 514,767, Oct. 15, 1974, Pat. No. 3,948,939, which is a continuation-in-part of Ser. No. 314,099, Dec. 11, 1972, Pat. No. 3,905,998, which is a continuation-in-part of Ser. No. 200,205, Nov. 18, 1971, Pat. No. 3,758,496, which is a continuation-in-part of Ser. No. 42,620, June 2, 1970, Pat. No. 3,687,969.

[52] U.S. Cl. .................... 260/315; 260/340.9; 424/274

[51] Int. Cl.$^2$ .............................. C07D 209/86
[58] Field of Search ............................ 260/315

[56] References Cited
UNITED STATES PATENTS 3,868,387  2/1975  Berger et al. .................. 260/315

*Primary Examiner*—Henry R. Jiles
*Assistant Examiner*—R. W. Ramsuer
*Attorney, Agent, or Firm*—Frederik W. Stonner; B. Woodrow Wyatt

[57] ABSTRACT

9-Benzoyl-3-hydroxymethyl-1,2,3,4-tetrahydrocarbazole and 9-benzoyl-3-(N-phenylcarbamoyloxymethyl)-1,2,3,4-tetrahydrocarbazole, having respectively antiinflammatory and antibacterial activities, and their preparation are described.

1 Claim, No Drawings

9-BENZOYL-1,2,3,4-TETRAHYDROCARBAZOLE

CROSS-REFERENCES TO RELATED APPLICATIONS

This application is a continuation-in-part of copending application Ser. No. 514,767, filed Oct. 15, 1974, now U.S. Pat. No. 3,948,939, issued Apr. 6, 1976, in turn a continuation-in-part of application Ser. No. 314,099, filed Dec. 11, 1972, now U.S. Pat. No. 3,905,998, issued Sept. 16, 1975, in turn a continuation-in-part of Ser. No. 200,205, filed Nov. 18, 1971, now U.S. Pat. No. 3,758,496, issued Sept. 11, 1973, in turn a continuation-in-part of Ser. No. 42,620, filed June 2, 1970, now U.S. Pat. No. 3,687,969, issued Aug. 29, 1972.

BACKGROUND OF THE INVENTION

1. Field of the Invention

The invention relates to 9-benzoyl-3-($CH_2OY$)-1,2,3,4-tetrahydrocarbazoles.

2. Description of the Prior Art

9-Benzoyl-1,2,3,4,-tetrahydrocarbazoles, having antiphlogistic, analgesic, antifebric and sedative properties, are described in British Patent Specification No. 1,183,093, published Mar. 4, 1970. 4-Hydroxymethyl-9-methyl-1,2,3,4-tetrahydrocarbazole, an intermediate for corresponding 4-aminomethyl compounds, is described in U.S. Pat. No. 3,752,823, issued Aug. 14, 1973.

SUMMARY OF THE INVENTION

The invention provides a composition of matter defined as a 9-benzoyl-3-($CH_2OY$)-1,2,3,4-tetrahydrocarbazole of the formula

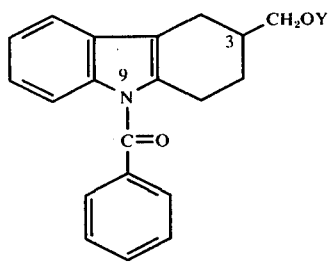

wherein Y is hydrogen or N-phenylcarbamoyl.

The compound of the invention having formula I wherein Y is hydrogen was found to be useful as an antiinflammatory agent when tested in pharmacological test procedures described hereinbelow.

The compound of the invention having formula I wherein Y is N-phenylcarbamoyl was found to be useful as an antibacterial agent when tested as described hereinbelow.

DETAILED DESCRIPTION OF THE INVENTION

The molecular structures of the compounds of the invention were assigned on the basis of the method of their synthesis and study of their infrared spectra, and confirmed by the correspondence between calculated and found values for the elementary analysis.

The compounds of the invention were prepared as follows:

EXAMPLE 1

9-Benzoyl-3-hydroxymethyl-1,2,3,4-tetrahydrocarbazole (formula I, Y=hydrogen)

1-Benzoyl-1-phenylhydrazine hydrochloride (23.8 g.) and 18 g. of 4-hydroxymethylcyclohexanone ethylene ketal in 450 ml. of absolute ethyl alcohol was heated under reflux for four hours. The chilled mixture was filtered, the filtrate was evaporated to dryness under reduced pressure and the resulting residue was dissolved in ether. The ether solution was washed with water, dilute hydrochloric acid, water, dilute sodium bicarbonate, and water, dried and evaporated to dryness to give, after recrystallization from ethyl acetate-hexane, 9.6 g. of 9-benzoyl-3-hydroxymethyl-1,2,3,4-tetrahydrocarbazole; m.p. 105°–107° C.

Preparation of 4-Hydroxymethylcyclohexanone ethylene ketal

Ethyl cyclohexanone-4-carboxylate (335 g.), 550 ml. ethylene glycol and 21 g. of p-toluenesulfonic acid in 5.5 liters of benzene were heated at reflux with stirring for 24 hours while water was separated by means of a water trap. The mixture was cooled and poured into 4 liters of ice water. The benzene layer was separated, washed with 1 liter of 5% sodium bicarbonate, 1 liter of water and 1 liter of saturated sodium chloride solution, dried and evaporated to dryness to give, after distillation, 245.6 g. of ethyl cyclohexanone-4-carboxylate ethylene ketal; b.p. 95°–99.5° C. (0.07 mm.); $n^{25}$ D 1.4620. A solution of 35 g. of the ketal-ester in 50 ml. of dry tetrahydrofuran was added dropwise to 5.7 g. of lithium aluminum hydride in 250 ml. of dry tetrahydrofuran, and the mixture was heated at reflux for five hours and cooled to room temperature. A saturated sodium chloride solution (11.4 ml.) was added dropwise and heating at reflux was continued for one hour. The mixture was cooled and filtered, and the filtrate was dried and evaporated to dryness to give 26.9 g. of 4-hydroxymethylcyclohexanone ethylene ketal as a clear, colorless oil which was used without further purification.

EXAMPLE 2

9-Benzoyl-3-(N-phenylcarbamoyloxymethyl)-1,2,3,4-tetrahydrocarbazole (formula I, Y = N-phenylcarbamoyl)

9-Benzoyl-3-hydroxymethyl-1,2,3,4-tetrahydrocarbazole (9.8 g.) and phenylisocyanate (4.2 g.) were combined and heated on a steam bath for one and one-half hours. The mixture was cooled and triturated in ether and the resulting solid was collected by filtration and washed with ether to give 7.1 g. of the title compound; m.p. 140°–143° C.

The antiinflammatory activity of 9-benzoyl-3-hydroxymethyl-1,2,3,4-tetrahydrocarbazole was determined by its ability to inhibit in rats carrageenin-induced foot edema and adjuvant-induced arthritis. A brief description of the pharmacological test procedures employed follows.

Inhibition of Carrageenin-Induced Foot Edema in Rats

Young male rats weighing 100–110 g. are used. Food is withdrawn approximately 18 hours prior to medication but the animals are permitted free access to drinking water up to the time of medication. Drugs to be tested are suspended by triturating in 1% gum tragacanth using ground glass homogenizers and administered by gavage in a volume of 1 ml/100 g body weight. Control animals receive the gum tragacanth only. One hour after medication, 0.05 ml of 1% suspension of carrageenin in 0.9% saline is injected into the plantar tissue of the left hind paw. Three hours after injection of the carrageenin, edema formation, i.e., increase in foot volume (difference between left hind paw and the uninjected right hind paw) is measured plethysmographically in the unanesthetized rat.

Inhibition Adjuvant-Induced Arthritis in Rats

Adult male rats weighing 200–230 grams are used. Adjuvant (M. butyricum), 0.1 ml of a 0.6% suspension in heavy mineral oil, is injected into the plantar tissue of the left hind paw. A negative control group is injected with mineral oil only. Beginning on the ninth day after adjuvant injection (polyarthritis does not appear until approximately the tenth day after adjuvant administration), the animals receive 6 daily medications of test compound suspended by triturating in 1% gum tragacanth using a ground glass homogenizer and administered by gavage in a volume of 1 ml/100 g body weight. Both the negative control and adjuvant injected control animals receive the vehicle only. Food and water are permitted ad libitum. Twenty-four hours after the last medication, the animals are weighed, the degree of arthritic involvement, i.e., increase in foot volume and plasma inflammation units are determined. Foot volume is measured plethysmographically in the unanesthetized rat.

9-Benzoyl-3-hydroxymethyl-1,2,3,4-tetrahydrocarbazole was found to be active when tested in rats at 100 mg./kg. of body weight in the Inhibition of Carrageenin-Induced Foot Edema and Adjuvant-Induced Arthritis Test Procedures described above and is indicated for use as an antiinflammatory agent. This compound can be prepared for use by following conventional pharmaceutical procedures; that is, it can be incorporated in unit dosage form in tablets or capsules for oral administration either alone or in combination with suitable adjuvants such as calcium carbonate, starch, lactose, talc, magnesium stearate, gum acacia, and the like; or as an aqueous or oil suspension or solution in a pharmaceutically acceptable vehicle such as aqueous alcohol, glycol, oil solution or oil water emulsion for oral or parenteral administration.

9-Benzoyl-3-(N-phenylcarbamoyloxymethyl)-1,2,3,4-tetrahydrocarbazole, when tested in the Autotiter method described by Goss et al., Applied Microbiology 16 (No. 9), 1414–1416 (1968), was found to be antibacterially effective against Pseudomonas aeruginosa at a concentration of 125 mcg./ml. thus indicating the utility of this compound as an antibacterial agent against Pseudomonas aeruginosa. This compound may be formulated for use by conventional procedures, e.g., for application to inanimate surfaces; it can be formulated as a dilute solution in an aqueous medium or in a solution containing a surfactant and is applied to the surface to be disinfected by conventional means such as spraying, swabbing, immersion and the like.

We claim:
1. 9-Benzoyl-3-(N-phenylcarbamoyloxymethyl)-1,2,3,4-tetrahydrocarbazole.

* * * * *